United States Patent
Gonzalez (10) Patent No.: US 6,685,729 B2
(45) Date of Patent: Feb. 3, 2004

(54) PROCESS FOR TESTING AND TREATING ABERRANT SENSORY AFFERENTS AND MOTORS EFFERENTS

(76) Inventor: George Gonzalez, 425 N. Gardner St., Los Angeles, CA (US) 90036

(*) Notice: Subject to any disclaimer, the term of this patent is extended or adjusted under 35 U.S.C. 154(b) by 401 days.

(21) Appl. No.: 09/912,197

(22) Filed: Jul. 24, 2001

(65) Prior Publication Data

US 2003/0018247 A1 Jan. 23, 2003

Related U.S. Application Data

(60) Provisional application No. 60/302,254, filed on Jun. 29, 2001.

(51) Int. Cl.[7] .............................. A61N 1/18; A61N 2/08; A61N 5/06
(52) U.S. Cl. .............................. 607/1; 607/89; 600/554
(58) Field of Search ................................. 128/897–898; 600/300–301, 372, 544, 546, 554, 555, 557; 601/1, 15; 607/1–3, 43, 46, 48–49, 88–89, 96, 98–100, 103, 115

(56) References Cited

U.S. PATENT DOCUMENTS

| | | | |
|---|---|---|---|
| 4,064,870 A | * 12/1977 | Dumitrescu et al. | ........ 600/554 |
| 4,340,063 A | 7/1982 | Maurer | |
| 4,671,285 A | * 6/1987 | Walker | ........ 607/89 |
| 4,731,051 A | 3/1988 | Fischell | |
| 4,926,865 A | 5/1990 | Oman | |
| 5,117,826 A | 6/1992 | Bartelt et al. | |
| 5,284,154 A | 2/1994 | Raymond et al. | |
| 5,464,436 A | * 11/1995 | Smith | ........ 607/89 |
| 5,549,118 A | * 8/1996 | John et al. | ........ 600/554 |
| 5,775,331 A | 7/1998 | Raymond et al. | |
| 5,797,854 A | 8/1998 | Hedgecock | |
| 5,843,142 A | 12/1998 | Sultan | |
| 5,861,015 A | 1/1999 | Benja-Athon | |
| 5,899,922 A | * 5/1999 | Loos | ........ 607/2 |
| 6,064,911 A | 5/2000 | Wingrove | |
| 6,132,360 A | 10/2000 | Halpern | |
| 6,209,545 B1 | 4/2001 | Zhukova et al. | |
| 6,267,733 B1 | * 7/2001 | Peterson et al. | ........ 600/587 |
| 6,302,900 B1 | * 10/2001 | Riggs | ........ 607/89 |
| 2001/0029391 A1 | * 10/2001 | Gluckman et al. | ........ 607/2 |

* cited by examiner

Primary Examiner—Kennedy Schaetzle
Assistant Examiner—Kristen Droesch
(74) Attorney, Agent, or Firm—Kelly Bauersfeld Lowry & Kelly, LLP (57) ABSTRACT

A process for treating aberrant sensory afferents and motor efferents includes performing a singular sensory or motor function test, and identifying an area of dysfunction. A nerve root and pathway to the area of dysfunction, a structural or biochemical component of the dysfunction, vascular supply to the area of dysfunction, blood supply/lymphatic drainage for the area of dysfunction, and viscera associated with the area of dysfunction is then identified. These areas are stimulated using the therapeutic device until retesting no longer detects any dysfunction. Neurological inhibition is identified by performing two or more sensory or motor function tests simultaneously. The therapeutic device is used to stimulate the area of dysfunction, spine and head until the neurological inhibition is no longer detected.

27 Claims, 3 Drawing Sheets

PROCESS FOR TESTING AND TREATING ABERRANT SENSORY AFFERENTS AND MOTORS EFFERENTS

RELATED APPLICATION

This application claims priority from Provisional Application Serial No. 60/302,254, filed Jun. 29, 2001.

BACKGROUND OF THE INVENTION

The present invention relates generally to the various tests in health care used to identify a diagnosis and subsequent treatment. More particularly, the present invention relates to a process for testing and treating neurological inhibition by resetting sensory afferent and motor efferent nerve supply to the area in which neurological inhibition is detected.

Currently, all health professionals are trained in the use of various tests (neurologic, orthopedic, physiologic, visceral or biochemical tests) for the purpose of identifying a diagnosis and treatment. All of the aforementioned tests are excellent for the purpose that they were created. In general, their purpose is to isolate and identify a breakdown of a specific function. If that function does not break down when isolated, it is considered normal. When there is a breakdown in a specific test or function, treatment is given locally to the area of involvement. That treatment may involve one or more of the following: surgery, medication, manipulations, therapy or exercise. One or more of the above treatments will be given until the specific test or functions are considered normal.

While the basic concepts of the health profession have been described, on a more detailed level, the following will explain more specific concepts and tests necessary for understanding the present invention.

The nervous system is the network in which the body communicates. The brain is the center of the nervous system and is protected by the skull. An extension of the brain is the brain stem and spinal cord, traveling from the base of the skull to the lower back. The spinal cord is protected by the spinal vertebra. Thee are seven cervical vertebra, twelve thoracic vertebra and five lumbar vertebra. Nerves extend outward from the right and left sides of the brain, brainstem (CN I–XII) and spinal cord to the entire body. Between each vertebra, the spinal cord extends a nerve which will give nerve supply to a specific area of the body. This extension from the spinal cord is called a nerve root and is named by the level of which it exits the spinal vertebra. All nerves are then further described by the side of the body that they innervate-right or left.

The basic flow of communication within the nervous system is Sensory (body to brain) and then Motor (brain to body), and then the cycle repeats itself. This creates two basic possibilities to have dysfunction in the body. First, a break down in the communication of the sensory pathway form the body to the brain. Second, a breakdown of the motor pathway communication from the brain to the body. Traditionally there are tests designed to challenge the integrity of various aspects of one of both of these communication pathways. Examples of the sensory tests would be those testing the five senses (sight, smell, taste, touch, hearing). An example of a motor test would be muscle strength. And example of both would be all deep tendon and pathological reflex tests.

This network of the nervous system extends throughout the entire body and is in constant communication with every cell in the body. External and internal stimuli are sensed and ascend toward the brain on afferent tracts. Afferent means traveling from the body toward the brain. The sensory information is processed in the spinal cord and brain and then motor commands descend to the body from the brain on efferent tracts. Efferent means traveling from the brain toward the body. The body will sense the change created by the motor commands and will send sensory information to the brain and the cycle will continue. These are the two basic channels of communication in the body, the first being the ascending sensory afferent tracts and secondly the descending motor efferent tracts.

Sensory Afferents

Every nerve in the body can receive sensory information. Only specialized nerves can receive special sensory information. The following is a list of the known sensory information recognized by the nervous system:

Vision—The ability to see (special sense of the eyes)
Smell—The ability to recognize odor (special sense of the nose)
Taste—The ability to recognize taste (special sense of the mouth)
Hearing—The ability to recognize sound (special sense of the ear)
Touch—To perceive by the tactile sense, to feel.
Light Touch—To perceive superficial tactile sense
Deep Touch—ability for deeper tissues to discern touch
Tactile Discrimination—The ability to localize two points of pressure on the surface of the skin and to identify them as discrete sensations.
Vibration—The ability to perceive vibrations transmitted through to the deep tissues.
Form Recognition—The ability to recognize from. Form is the size, shape and external appearance of anything.
Joint and Muscle Sensation—The ability to sense join and muscle position.
Conscious and Unconscious Proprioception—the concept of the nervous systems ability to be constantly aware of its posture, movement, changes in equilibrium, weight, resistance to itself and other objects relating to the body.
Pressure—Stress of force exerted on a body, as by tension, weight or pulling.
Pain—The sensory and emotional experience associated with actual or potential tissue damage. Thus, pain includes not only the perception of an uncomfortable stimulus but also the response to that perception.
Temperature—The ability to recognize hot and cold
Coordination of Movements and Posture—The ability to coordinate movement and posture.

The following is a list of Cranial Nerves (CN) that send afferent sensory information form the body to the brain.
CN I—Olfactory Nerve—The special sense of smell
CN II—Optic Nerve—The special sense of vision
CN V—Trigeminal Nerve—Sensory information of the face eye nasal and oral cavities
CN VII—Facial Nerve—The special sense of taste and contributes the sense of hearing
CN VIII—Vestibulocochlear Nerve—The special sense of hearing, equilibrium and balance
CN IX—Glossopharyngeal Nerve—The special sense of taste, it also monitors blood pressure and oxygen and carbon dioxide levels of the blood, sensory information from the ear, tongue, tonsils, pharynx.
CN X—Vagal Nerve—Sensory information of the dura, ear, pharynx, larynx, thoracic and abdominal viscera and innervate the taste buds in the epiglottis.

The following is a list of sensory afferent nerve tracts that send afferent sensory information from the body to the brain.

Dorsal Columns—mediates tactile discrimination, vibration, form recognition, join and muscle sensation, and conscious proprioception.

Ventral Spinal Thalamic Tract—mediates light touch.

Lateral Spinal Thalamic Tract—mediate fast and slow pain fibers and temperature (hot and cold)

Dorsal Spinalcerebellar Tract—mediates unconscious proprioceptive information

Ventral Spinalcerebellar Tract—mediates unconscious proprioceptive information and coordinates movements and posture of the entire lower extremity.

Cuneocerebellar Tract—Mediates unconscious proprioceptive information and coordinates movement and posture of the entire upper extremity.

Testing Sensory Function

Testing sensory function is based on traditional techniques. The goal is to test the ability and quality of the sensory afferents. Tests are usually performed on the right and left side individually. Examples include but are not limited to:

Vision—color, acuity, depth, blind spot, visual and spatial recognition

Smell—recognize different odors

Taste—recognize and localize taste, bitter, sour, sweet, salty

Hearing—recognize, localize and repeat sound, vibration via bone conduction verses air conduction Touch—To perceive by the tactile sense, dull, sharp, rough, smooth.

Light Touch—To perceive superficial tactile sense.

Deep Touch—ability for deeper tissues to discern touch

Tactile Discrimination (Two Point Discrimination)—The ability to localize two points of pressure on the surface of the skin and to identify them as discrete sensations.

Vibration—The use of tuning forks or percussive stimulation on different parts of the body and the patient recognizing that stimulation.

Form Recognition—The ability to recognize form. Usually tested by placing a key or coin in the hand of the patient and asking them to identify and describe the size, texture and shape of the object.

Joint and Muscle Sensation—Various orthopedic, neurologic and physical stress tests Conscious and Unconscious Proprioception and Coordination of Movements and Posture—this is tested by various methods which challenge the patient's ability to recognize and locate parts of their body with their eye closed. These tests are most commonly referred to as the drunk driving type tests, for example asking the patient to touch their finger to their nose with their eyes closed.

Pressure—Patient is asked to identify, localize and describe different stresses or force exerted on a body, a by tension, weight or pulling.

Pain—Patient is asked to identify, localize and describe different types of pain. The pain stimulus is usually applied by the doctor as localized pressure or the use of a sharp pin or pinwheel.

Temperature—The ability to recognize, localize and describe hot and cold.

Motor Efferents

Every nerve in the body can receive motor stimulus from the brain and spinal cord. The following is a list of the known motor efferents acting through the Cranial Nerve (CN:

CN III—Occulomotor Nerve—Governs Movements of the eyes and surrounding structure, and the ability to accommodate vision to distance and light CN IV—Trochlear Nerve—Governs Movement of the superior-oblique muscle CN V—Trigeminal Nerve—Innervate the muscles of mastication, ear and throat muscles CN VI—Abducent Nerve—Abducts the eye CN VII—Medicate facial muscles, salivation, lacrimination, tympanic membrane tone CN VIII—Vestibulocochlear Nerve—Contributes to balance and equilibrium CN IX—Glossopharyngeal Nerve—Salivation, gag reflex, contributes to swallowing CN X—Vagal Nerve—Innervate all muscles relating to swallowing, speaking, and innervate the viscera of the neck thoracic and abdominal cavities.

CN XI—Accessory Nerve—Innervate muscles which allow head and should movement

CN XII—Hypoglossal Nerve—Innervate muscles of the tongue.

The following is a list of the known motor efferents acting through the descending motor efferents:

Lateral Corticospinal (pyramidal) tract—controls volitional skilled motor activity Rubrospinal Tract—controls flexor tone Vestibulospinal Tract—controls extensor tone Descending Autonomic Tracts—project to sympathetic and parasympathetic centers of the spinal cord.

Testing Motor Function

Traditional techniques for testing the integrity and quality of the motor efferents are usually tested on the right and left side individually. They include but are not limited to:

Orthopedic tests—structural stress tests designed to test the integrity of a joint of muscle or movement.

Neurologic tests—tests designed to test the integrity of the communication between the nervous system and the body. This includes testing the strength of a muscle as well as the reflex responses of the muscle. Most Neurologic tests are actually testing both sensory afferents and motor efferents and the result of the test will tell us if there is a sensory or motor problem.

Physiologic tests—tests signs and maneuvers that are performed to look for a physiologic response. These tests are also categorized by various orthopedic and neurologic texts.

Visceral tests—can be external or internal palpation, application of pressure or other stimulation.

Biochemical—are tests designed to measure function of the body usually by testing fluids or sample from the body (saliva, blood, urine, stool, etc.)

Treating Sensory and Motor Function

Currently all health professionals are trained in the use of the above-mentioned tests for the purpose of identifying a diagnosis and treatment. All of the aforementioned tests are excellent for the purpose that they were created. In general that purpose is to isolate and identify a breakdown of a specific function. If that function does not breakdown when isolated, it is considered normal. When there is a breakdown in a specific test of function, treatment is given locally to the area of involvement. That treatment may involve one or more of the following: surgery, mediation, manipulations, therapy or exercise. One or more of the above treatments will be given until the specific test or functions are considered normal. However, many people consider conventional treatments, particularly surgery and some forms of medication, to be extremely invasive or even debilitating.

Although current conventional tests are generally adequate in determining sensory or motor dysfunctions, it has been found that there may be hidden levels of dysfunction which are not detected using these tests alone. This dysfunction occurs within the nervous system. The dysfunction is caused by the improper inhibition of one or more of the functions being tested. This neurological dysfunction is hidden because of the manner in which patients are tested. Classically, a singular test (such as a neurologic, orthopedic, physiologic, visceral or biochemical test) is performed. When the patient can perform that singular event, the tested function is considered normal. However, in life patients perform multiple events simultaneously. It has been found that when two or more functions are tested simultaneously, more accurate information regarding the physical function is determined than a singular test alone. In fact, if the patient cannot perform two or more functions simultaneously, this uncovers the hidden neurological dysfunction of improper neurological inhibition.

Accordingly, there is a need for a process for testing and identifying areas of dysfunction and correcting such dysfunctions which are less invasive and debilitating than current methods. What is also needed is a process for testing and identifying neurological inhibitions. Such a process should provide treatment by resetting sensory afferent and motor efferent nerve supply to the area or physical function in question. The present invention fulfills these needs and provides other related advantages.

SUMMARY OF THE INVENTION

The present invention resides in a process for treating aberrant sensory afferents and motor efferents. The process involves testing for a physical function by performing a singular sensory or motor function test, and identifying an area of dysfunction. The singular sensory or motor test may include one of a neurologic, orthopedic, physiologic, visceral or biochemical test. Corrections are performed for the dysfunction until retesting no longer detects any dysfunction. Such correction is typically performed by first identifying at least one of a nerve root and pathway to the area of dysfunction, a structural or biochemical component of the dysfunction, vascular supply to the area of dysfunction, blood supply/lymphatic drainage for the area of dysfunction, and viscera associated with the area of dysfunction. Tissue or bone that entraps a vein, artery or nerve associated with the dysfunction is typically manipulated to release pressure or blockage.

The stimulation is typically performed using a therapeutic device. Although a light generator in the form of laser is preferred, other therapeutic devices can be used as well. For example, a therapeutic device emitting electrical stimulation, sound waves, vibration, pressure, magnetic flux or that which alters temperature may be used.

When the physical dysfunction is no longer detected, neurological inhibition is tested and identified by performing a combined test. Such a combined test comprises performing at least two sensory or motor function tests simultaneously. Sensory afferent and motor efferent nerve supply to the area or physical function being tested is reset by performing corrections for the neurological inhibition until no neurological inhibition is detected. Such correction is performed using the therapeutic device to stimulate the area of dysfunction, spine and head. This correction is performed until the neurological inhibition is no longer detected, or improvement is achieved.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is a flow chart illustrating the steps taken in identifying neurological inhibition and correcting the same in accordance with the present invention.

DETAILED DESCRIPTION OF THE PREFERRED EMBODIMENTS

The present invention resides in a process for testing and treating aberrant sensory afferents and motor efferents. The methodology of this process consists of two sub-processes, referred to in the written description and drawings herein as Process A and Process B. Each process consists of testing for dysfunction, a treatment for the dysfunction, and then re-testing to verify the result of the treatment. The goal of this treatment process is to maximize human performance. To do this, the primary focus is to ensure that the entire body has the highest utilization of its nervous system.

The following is a list of definitions and concepts which are intended to aid the reader in understanding the methodology of testing and treating according to the present invention.

Stimulus

1. Any agent or factor able to influence living protoplasm directly, as one capable of causing muscular contraction or secretion in a gland, or of initiating an impulse in a nerve. 2. A change of environment of sufficient intensity to evoke a response in an organism. 3. An excitant or irritant.

Response

1. A reaction, such as contraction of a muscle or secretion of a gland, resulting form a stimulus. 2. The sum total of reactions of an individual to specific conditions, e.g., the response (favorable or unfavorable) of a patient to a certain treatment.

Activation

Is defined as to make active. To expand on the definition we will use this term to mean: to engage a system to a higher level of function, or to remove inhibition.

Inhibition

Is defined as a repression or restraint of a function.

Stress

In medicine, the result produced when a structure, system, or organism is acted upon by forces that disrupt, equilibrium or produce strain. In health care, the term denotes the physical (gravity, mechanical force, pathogen, injury) and psychological (fear, anxiety, crisis, joy) forces that are experienced by individuals. It is generally believed that biological organisms require a certain amount of stress in order to maintain their well-being. [Gravity, light, darkness, physical resistance, etc . . . ]. However when stress occurs in quantities that the system cannot handle, it produces pathological changes.

Nervous systems Energy Capacity

The sum total of the nervous systems ability to do work, at any moment in time.

Exceeding the Nervous Systems Energy Capacity

The concept of, one singular neurological event or the sum total of many neurological events, surpassing the nervous system's energy capacity causing inhibition of the entire nervous system. It is at this moment when aberrant rhythmic patterns, aberrant functions, and injuries can occur.

Neurological Overload

This is a concept that the nervous system has a limited energy capacity at any one moment of time. If the body exceeds the nervous system's energy capacity for a sustained period of time, a neurological overload will occur. Through neurological overload, the nervous system will conserve its energy by inhibiting the functions that consume the most neurological energy.

Internal Regulation System

The internal regulation system is a critical component of the central core of neurons and pathways that control automatic functions necessary for life and survival of the species. The internal regulation system controls visceral, endocrine, and behavioral functions that maintain the internal environment of the body in response to internal and external changes. The neural components are located supratentorial, posterior fossa, spinal, an peripheral levels. The most important functions of the internal regulation system are: (1) maintenance of homoeostasis, or the internal environment, for cell function; (2) integration of adaptive response to external and internal stimuli, ongoing reaction to fear and stress; (3) drinking, feeding, sexual behavior; (4) modulation of pain sensation; and (5) regulation of immune function. Th internal regulation system performs all these important functions through three components; (1) the autonomic nervous system, including pathways innervating the hard, smooth muscle, visceral organs, blood vessels, skin, and eyes; (2) the neuroendocrine system, including circulating hormones from the pituitary gland and the peripheral endocrine organs; and (3) connections with the somatic motor system for expression of complex behaviors such as feeding and drinking and of automatic motor functions such as respiration and swallowing.

The internal regulating system is an example of how the nervous system is in a state of constant communication with every cell in the body. The brain receives information from the sensory afferents and the input mechanisms of the internal regulation system, and the brain responds via the motor efferents and the output mechanism of the internal regulation system. It is through this constant feedback mechanism that the nervous system generates rhythmic patters in which the body functions.

Examples of function regulated by the internal regulation system include but are not limited to: visual sensation, visceromotor coordination (heart rate, peristalsis, respiration, etc.), emotional response, homeostasis, hormone control, arousal, circadian rhythms, reproduction cycles, respiration, integration of brainstem reflexes, sympathetic and parasympathetic tone, blood temperature, pH, osmolarity of oxygen and carbon dioxide in the blood, glucose levels, automatic motor patterns (chewing, walking etc.)

Neurological Recognition

Neurological Recognition is based on the concept that the nervous system is in constant communication with every cell in the body. This communication functions through the rhythmic patterns. As long as the ranges of these rhythmic patterns are not interrupted, the rhythm will remain. If the nervous system recognizes that a rhythmic pattern is aberrant it will change its function to normalize the pattern. If the nervous system does not recognize the aberrant rhythm it will remain aberrant. The reason it remains aberrant is because the nervous system has an "if it is not broken, do not fix it" attitude. Therefore, if the nervous system does not recognize an aberrant function (sensory, motor, gate pattern, proprioceptive patterns, reciprocal inhibition pattern, infection, manifestation, tissue damage, etc.) there will be no action taken to fix or fight off these problems. In the methodology presented it is a goal to make the nervous system aware of the aberrant function and stimulate the body to reset its rhythmic patterns associated with those functions.

Figure 1:
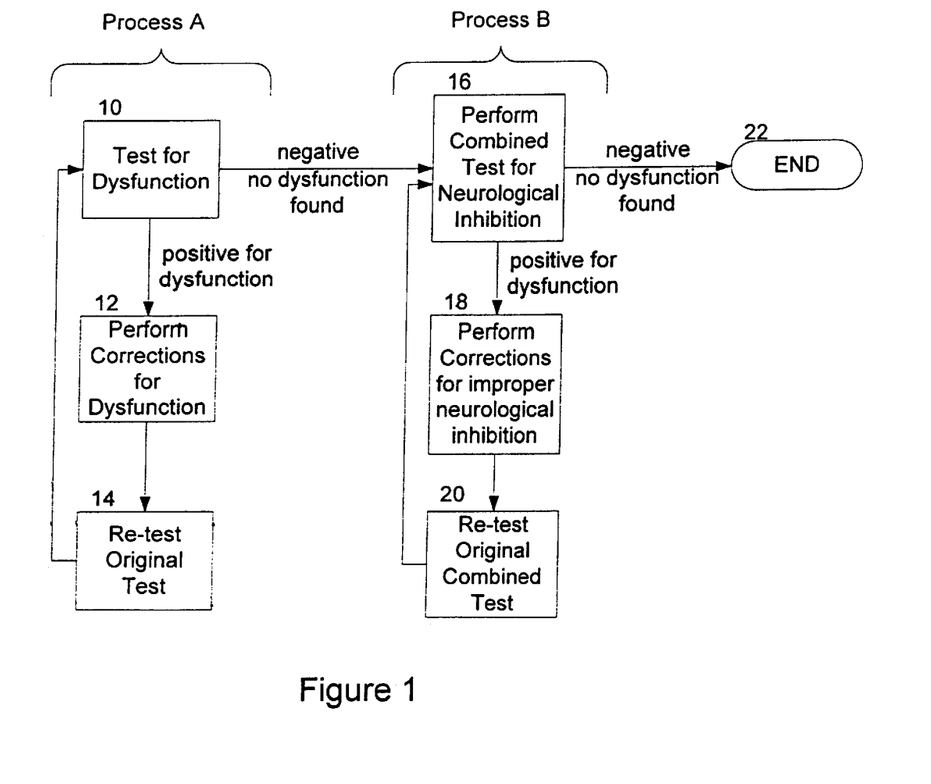
FIG. 1 is a flow chart illustrating the general steps taken in accordance with the present invention.

Referring now to FIG. 1, the general steps in the overall process of the present invention is illustrated. As a first step in Process A, a test is performed to determine dysfunction (10). If the test is positive for the dysfunction, corrections are performed for the dysfunction (12). The original test is then re-tested (14) until the test is negative and no dysfunction is found. As a first step in Process B, a combined test is performed to determine neurological inhibition (16). If the test is negative and no dysfunction is found, no other steps are taken. However, if the test is positive for neurological inhibition dysfunction, corrections are performed to improve or even remove the improper neurological inhibition (18). The original combined test is then re-tested (20), and this process repeated until the test is negative and no neurological inhibition is found or significant improvement is determined at which point the process ends (22).

Figure 2A:
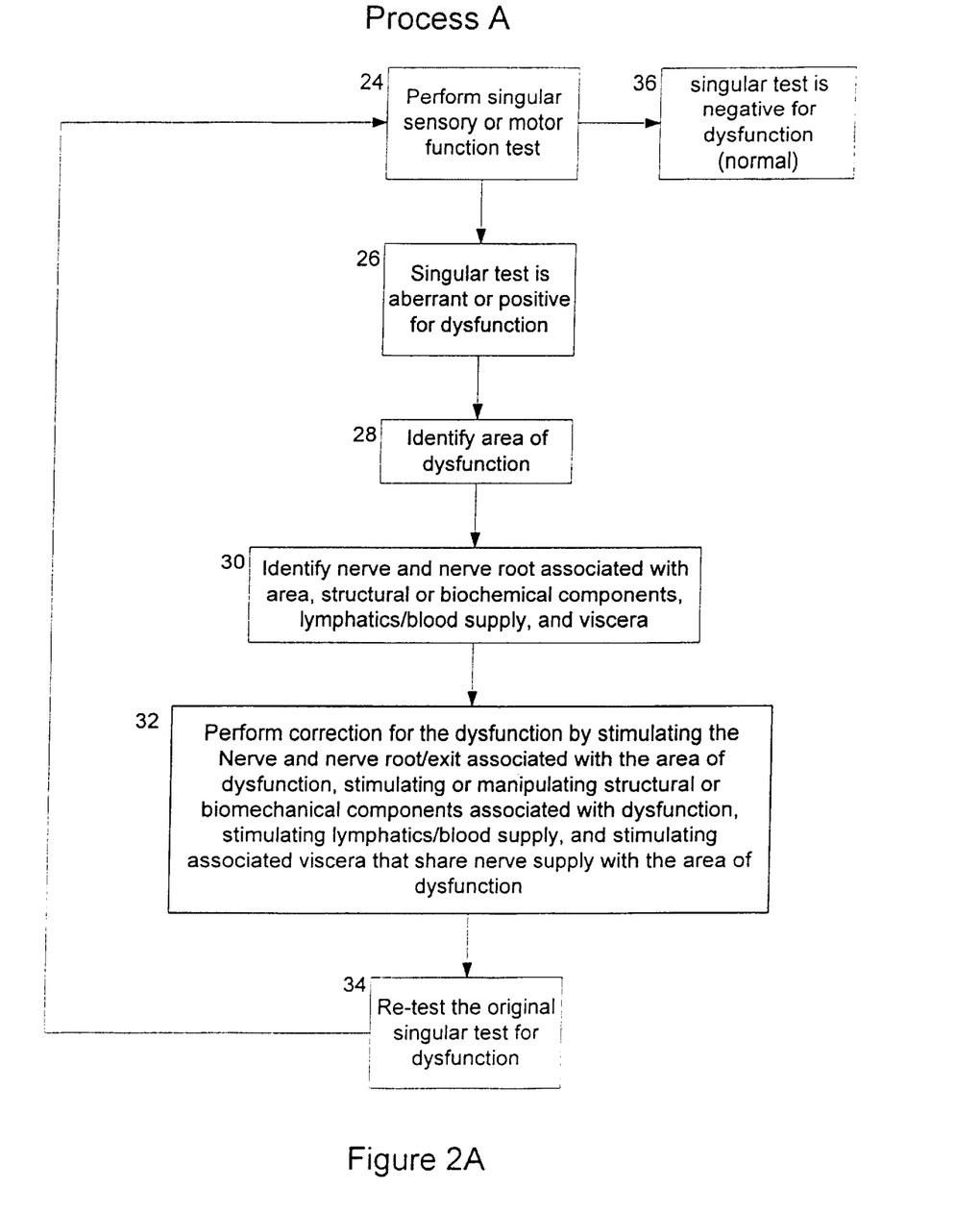
FIG. 2 is a flow chart illustrating the steps taken to identify and correct a physical dysfunction in accordance with the present invention.
Figure 2B:
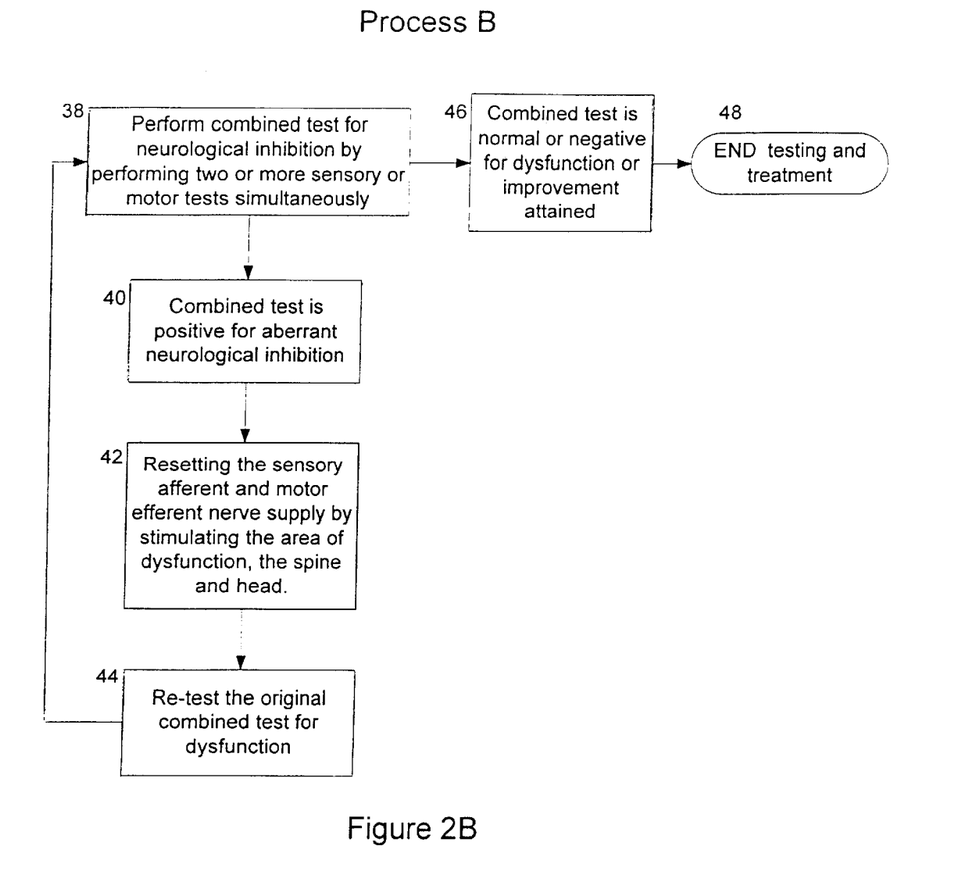

With reference to FIG. 2, the invention will be described with more particularity. FIG. 2, illustrates the steps taken in Process A which tests, identifies and corrects a physical dysfunction. For purposes of the invention, physical function refers to any sensory or motor function. The first step consists of performing a singular traditional sensory or motor function test (24). Testing a sensory and motor function has been described above and includes neurologic, orthopedic, physiologic, visceral, and biochemical tests. Other sensory or motor function tests may also be used. If the singular test is aberrant or positive for the dysfunction (26), the area of dysfunction is identified (28).

At this point, for exemplary and explanation purposes only, a right shoulder dysfunction with a C5 myotome of the deltoid muscle will be described. However, it should be understood that any other body part and associated test can be interchanged for the right shoulder and C5 myotome. A myotome test is a neurological evaluation of one nerve that exits the spine and innervates a specific area of the body. A myotome is tested by evaluating the strength of a muscle(s) innervated by that specific nerve.

Myotomes are graded for strength on a scale of 1 to 5

0=paralysis

1=muscle fasciculation without movement

2=movement in the absence of gravity (as when laying down)

3=movement while in gravity, but without resistance

4=movement with gravity and some resistance

5=full strength against gravity and resistance

Any weakness, below grade 5, of the right deltoid muscle would indicate a dysfunction of the C5 nerve. This dysfunction may have various causes, which must be addressed in order to function properly.

The treatment of the dysfunction according to the invention comprises identifying nerve root and pathway to the area of dysfunction, a structural or biochemical component of the dysfunction, vascular supply to the area of dysfunction, blood supply/lymphatic drainage for the area of dysfunction and viscera associated with the area of dysfunction (30). Thus, in order to treat the dysfunction of the C5 myotome in our example, there are five issues that need to be addressed.

1. Neurologic involvement
2. Structural or biomechanical alignment
3. Lymphatic back-up
4. Viscera (organs and glands) that share the same nerves as the functions being tested.
5. Neurologic Inhibition (which is tested and treated in Process B).

Corrections are performed for the dysfunction by stimulating the nerve associated with the dysfunction, the structural or biochemical component of the dysfunction, the vascular supply associated with the dysfunction, and the blood/lymphatics and viscera associated with the area of dysfunction (32). Stimulation of the nervous system can be performed by anything that is sensed by the nervous system. This includes but is not limited to: light generators (colors, light emitting diodes, lasers, etc), sound generators (ultrasound, speakers, tuning forks, etc.), taste stimulation (foods, chemical, etc.), olfactory stimulation (odors, terpines, anything that stimulate the sense of smell, etc), electric stimulators (TENS, MENS, electric muscle stimulation, etc.), vibration stimulators (percussion instruments, tuning forks, etc), temperature generators (hot packs, cold packs, diathermy, etc.), and pain stimulators (pin, pinwheel, etc.). A coherent laser light is the most convenient and comprehensive form of stimulation for treating the nervous system. The therapeutic device that has been found to perform the most effective treatment of this system is the Erchonia laser manufactured by Tuco Innovations. It is a 10 milliwatt, 635 nanometer diode laser. However, any therapeutic device that provides stimulation that the nervous system can identify can be used to correct the dysfunctions mentioned herewithin.

Referring back to our example, all neurologic projections of the C5 myotome are stimulated in order to treat the neurologic involvement. This includes the C5 nerve root and nerve, muscles and viscera innervated by C5, and the associated cerebellum and cortex. In this example, the right cerebellum and the left cortex control the right C5 myotome. The dysfunction can be caused by a dysfunction in any one of the C5 nerve projections. The way to improve the nerves ability to function is by stimulation. Any therapeutic device can perform this stimulation. The most effective being pulsed or non-pulsed laser light.

Structural or biochemical alignment is then treated. This involves the physical manipulation of tissue or bone that is entrapping the vein artery and or nerve. Using the original test as our guideline, we start at the spine where the nerve exits and contact the spine. We apply force to the left, while retesting the C5 myotome. We continue to apply force in different directions (right, left, up, down, etc.), until we find an improvement in the tested myotome. This can be repeated over any part of the body that can entrap or inhibit the function of the C5 nerve.

The lymphatic back-up and other drainage areas, including the blood supply, is then treated. When an area of the body is injured or rehabilitating it must detoxify properly. Any toxin or debris that cannot pass through the artery and veins capillary system must be carried out by the lymphatic system. Stimulating can be performed to encourage motility of the lymphatic system. The lymphatic system has two main areas before it dumps its contents into the heart, the right and left thoracic duct. A backup of the right thoracic duct will block lymphatic drainage of the right arm, chest and right side of the head. A backup of the left thoracic duct will block lymphatic drainage of the left side of the head, chest and arm as well as the abdomen and both legs. To encourage lymphatic motility stimulation is done from the furthest point of the body toward the heart. The main lymphatic channels are located on both inner legs and inguinal regions, the center fo the abdomen, axilla, and pectoral area, as well as both sides of the neck. For this example we will need to stimulate the right neck, axilla and pectoral areas toward the heart to encourage lymphatic motility. Any therapeutic device can perform the stimulation. The most effective being pulsed or non-pulsed laser light.

Viscera, organs and glands, that share the same nerves as the functions being tested are then treated. In this example, the C5 myotome weakness tells us that the C5 nerve is dysfunctional in some way. Therefore all the projections of that nerve will be affected. The cause of the nerve dysfunction can come from any of the projections of the C5 nerve. Stimulation can encourage the function of the associated viscera. Any therapeutic device can perform the stimulation. The most effective being pulsed or non-pulsed laser light.

The original test is then re-tested (34), in this case the C5 myotome test is repeated. An evaluation of strength is re-assessed, and an improvement in the original test after treatment indicates that the treatment was effective.

After arriving at a negative singular test result indicating normal physical function (36), the second process of the invention, Process B, is performed. With reference now to FIG. 3, a combined test is performed to determine neurological inhibition (38). This is done by performing two or more sensory or motor functions tests simultaneously. Although the patient may be able to perform each singular sensory or motor function test individually, the patient may be unable to perform the two or more simultaneous tests. This indicates aberrant neurological inhibition of one or more of the functions being tested. This hidden level of dysfunction may occur not only during what is classically known to be aberrant function, but also between the stage of what is considered normal and optimal function. This dysfunction occurs within the nervous system. The dysfunction is caused by the improper inhibition of one or more of the functions being tested.

An everyday example of improper inhibition would be driving a car with the emergency brake set. It does not matter how much you press on the gas pedal; your car will not express its maximum speed potential, because the emergency brake is inhibiting the cars acceleration. But in removing the improper inhibition, in this case the emergency brake, the car can function optimally. This is a simple analogy, but it explains the concept of improper inhibition.

This neurological dysfunction is hidden because of the manner in which we test patients. Classically we test a singular (neurologic, orthopedic, physiologic, visceral or biochemical) event. When the patient can perform that singular event, the tested function is considered normal. In life, patients perform multiple events simultaneously. Therefore, we should test multiple events simultaneously. When we test two or more functions simultaneously we are performing a dynamic test. This will give us more accurate information of function than a singular test alone. If the patient cannot perform two or more functions simultaneously, this uncovers the hidden neurological dysfunction of improper inhibition described earlier.

The present invention is a unique method that tests the nervous system's ability to handle multiple tasks simultaneously.

For explanation purposes, we will continue using the C5 myotome for the deltoid as the exemplary test and function test throughout this document. Keep in mind that any test can be used in place of the C5 myotome.

The following are examples of two or more tests performed simultaneously:

- C5 myotome—with any passive, active, resisted or stretched range of motion;
- L1 dermatome—with deep tendon or pathological reflex test;
- L4 reflex—while activating or testing of the cranial nerves;
- Hot pack on knee—with any other myotome or dermatome test;
- CN VII—while stimulating any part of the body to test neurological function i.e., pain, temperature, vibration, color, pressure, proprioception, coordination, sympathetic or parasympathetic responses, smell, taste, sound, tactile sense, etc.
- Resisted neck flexion—with any orthopedic test
- Psoas stretch—with any visceral test
- See the color red—with any biochemical test Process B involves the unique concept of performing two separate test simultaneously. For explanation purpose we will use right C5 myotome test for the deltoid muscle and the right L1, 2, 3 myotome test of the psoas muscle. Keep in mind that any test can be used in place of either of the above tests.

The C5 myotome test and L1, 2, 3 myotome test are to be preformed simultaneously. If one or more of these show dysfunction, it identifies the hidden aberrant neurological inhibition within one or more of the tested functions. This inhibition occurs during dysfunction, but it also may occur during what is consider normal function and optimal function.

When there is an aberrant neurological inhibition or neurological overload in the body, the sensory afferent and motor efferent nerve supply to the areas or functions being tested must be reset. The goal is to reestablish the proper rhythmic patterns associated to the areas or functions being tested. This is achieved by performing corrections for the neurological inhibition using a therapeutic device to stimulate the area of dysfunction, spine and head (42). It is recommended that the correction be performed within a few minutes of the two or more simultaneous tests.

Any therapeutic device can perform the stimulation. The most effective being pulsed or non-pulsed laser light. To perform the correction one or more of the following area needs to be stimulated: the area being tested, nerve and nerve root associated to the tested area, the entire spinal cord from coccyx to occiput, the entire brain stem, cerebellum, corpus callosum (via the apex of the head), glabella, right and left cortex, right and left mastoid processes, and right and left temporal mandibular joints. By doing this with the pulsed or non-pulsed laser it will correct the body's rhythmic pattern associated with the function being tested. After the treatment, the patient will have an improved ability to perform the two or more tests simultaneously.

The original combined test for the dysfunction is re-tested (44). In this example, the C5 myotome and the L1, 2, 3 myotome were tested simultaneously. Once the original test is repeated, an evaluation of dysfunction is re-assessed. If the combined test for the dysfunction is negative, or normal this improvement in the original test after treatment indicates that the treatment was effective (46) and the treatment comes to an end (48).

It will be appreciated by those skilled in the art that the present invention provides a means for discovering hidden neurological dysfunctions. Such dysfunctions can adversely affect the patient, but up until now have been difficult or even impossible to reveal. The present invention provides a process which not only uncovers these hidden dysfunctions, but provides a method for treating these dysfunctions in a quick and non-invasive manner.

Although several embodiments have been described in detail for purpose of illustration, various modifications may be made without departing from the scope and spirit of the invention. Accordingly, the invention is not to be limited, except as by the appended claims.

What is claimed is:

1. A process for treating aberrant sensory afferents and motor efferents, comprising the steps of:
   - testing for a physical function and identifying an area of dysfunction;
   - performing corrections for the dysfunction and retesting for the dysfunction until no dysfunction is detected;
   - testing for and identifying a neurological inhibition by performing a combined test; and
   - resetting sensory afferent and motor efferent nerve supply to the area or physical function being tested by performing corrections for the neurological inhibition until no neurological inhibition is detected.

2. The process of claim 1, wherein the step of testing for the physical function includes the step of performing a singular sensory or motor function test.

3. The process of claim 2, wherein the singular sensory or motor test includes one of a neurologic, orthopedic, physiologic, visceral or biochemical test.

4. The process of claim 2, wherein the combined test comprises performing at least two sensory or motor function tests simultaneously.

5. The process of claim 1, including the step of identifying at least one of a nerve root and pathway to the area of dysfunction, a structural or biochemical component of the dysfunction, vascular supply to the area of dysfunction, blood supply/lymphatic drainage for the area of dysfunction, and viscera associated with the area of dysfunction.

6. The process of claim 5, wherein the performing corrections for the dysfunction step comprises stimulating the nerve associated with the dysfunction, the structural or biochemical component of the dysfunction, the vascular supply associated with the dysfunction, and the blood supply/lymphatics and viscera associated with the area of dysfunction.

7. The process of claim 6, including the step of physically manipulating tissue or bone that entraps a vein, artery or nerve associated with the dysfunction.

8. The process of claim 6, wherein the resetting step includes the step of stimulating the area of dysfunction, spine and head.

9. The process of claim 8, wherein the stimulating step is performed through the use of a therapeutic device.

10. The process of claim 9, wherein the therapeutic device comprises a light generator.

11. The process of claim 10, wherein the light generator comprises a laser.

12. The process of claim 9, wherein the therapeutic device emits electrical stimulation.

13. The process of claim 9, wherein the therapeutic device emits sound waves.

14. The process of claim 9, wherein the therapeutic device emits vibration and pressure.

15. The process of claim 9, wherein the therapeutic device comprises a temperature generator.

16. The process of claim 9, wherein the therapeutic device emits magnetic flux.

17. A process for treating aberrant sensory afferents and motor efferents, comprising the steps of:

testing for a physical function by performing a singular sensory or motor function test and identifying an area of dysfunction;

performing corrections for the dysfunction using a therapeutic device and retesting for the dysfunction until no dysfunction is detected;

testing for and identifying a neurological inhibition by performing a combined test comprising at least two sensory and motor function tests simultaneously; and resetting sensory afferent and motor efferent nerve supply to the area or physical function being tested by performing corrections for the neurological inhibition using a therapeutic device until no neurological inhibition is detected.

18. The process of claim 17, wherein the singular sensory or motor test includes one of a neurologic, orthopedic, physiologic, visceral or biochemical test.

19. The process of claim 17, including the step of identifying at least one of a nerve root and pathway to the area of dysfunction, a structural or biochemical component of the dysfunction, vascular supply to the area of dysfunction, blood supply/lymphatic drainage for the area of dysfunction, and viscera associated with the area of dysfunction.

20. The process of claim 19, including the step of physically manipulating tissue or bone that entraps a vein, artery or nerve associated with the dysfunction.

21. The process of claim 19, wherein the performing corrections for the dysfunction step comprises using the therapeutic device to stimulate the nerve associated with the dysfunction, the structural or biochemical component of the dysfunction, the vascular supply associated with the dysfunction, and the blood supply/lymphatics and viscera associated with the area of dysfunction.

22. The process of claim 17, wherein the resetting step includes the step of stimulating the area of dysfunction, spine and head using the therapeutic device.

23. The process of claim 17, wherein the therapeutic device emits at least one of light, electrical stimulation, sound waves, vibration, pressure, temperature, or magnetic flux.

24. A process for treating aberrant sensory afferents and motor efferents, comprising the steps of:

testing for a physical function by performing a singular sensory or motor function test and identifying an area of dysfunction;

identifying at least one of a nerve root and pathway to the area of dysfunction, a structural or biochemical component of the dysfunction, vascular supply to the area of dysfunction, blood supply/lymphatic drainage for the area of dysfunction, and viscera associated with the area of dysfunction;

performing corrections for the dysfunction using a therapeutic device to stimulate the nerve associated with the dysfunction, the structural or biochemical component of the dysfunction, the vascular supply associated with the dysfunction, and the blood supply/lymphatics and viscera associated with the area of dysfunction and retesting for the dysfunction until no dysfunction is detected;

testing for and identifying a neurological inhibition by performing a combined test comprising at least two sensory and motor function tests simultaneously; and resetting sensory afferent and motor efferent nerve supply to the area or physical function being tested by performing corrections for the neurological inhibition using a therapeutic device to stimulate the area of dysfunction, spine and head until no neurological inhibition is detected.

25. The process of claim 24, wherein the singular sensory or motor test includes one of a neurologic, orthopedic, physiologic, visceral or biochemical test.

26. The process of claim 24, including the step of physically manipulating tissue or bone that entraps a vein, artery or nerve associated with the dysfunction.

27. The process of claim 24, wherein the therapeutic device emits at least one of light, electrical stimulation, sound waves, vibration, pressure, temperature, or magnetic flux.

* * * * *